(12) United States Patent
Haryadi et al.

(10) Patent No.: US 6,258,038 B1
(45) Date of Patent: Jul. 10, 2001

(54) METHODS OF NON-INVASIVELY ESTIMATING INTRAPULMONARY SHUNT FRACTION AND MEASURING CARDIAC OUTPUT

(75) Inventors: Dinesh G. Haryadi, Bangalore (IN); Joseph A. Orr, Park City, UT (US); Kai Kück, Hamburg (DE); Michael B. Jaffe, Cheshire, CT (US)

(73) Assignee: NTC Technology, Inc., Wilmington, DE (US)

( * ) Notice: Subject to any disclaimer, the term of this patent is extended or adjusted under 35 U.S.C. 154(b) by 0 days.

(21) Appl. No.: 09/465,059

(22) Filed: Dec. 16, 1999

Related U.S. Application Data

(62) Division of application No. 09/150,450, filed on Sep. 9, 1998, now Pat. No. 6,042,550.

(51) Int. Cl.[7] ................................................ A61B 5/02
(52) U.S. Cl. ..................... 600/504; 600/481; 600/483; 600/484; 600/526
(58) Field of Search ................................ 600/481, 483, 600/504, 508, 526, 538

(56) References Cited

U.S. PATENT DOCUMENTS

| | | |
|---|---|---|
| 4,221,224 | 9/1980 | Clark . |
| 4,463,764 | 8/1984 | Anderson et al. . |
| 5,060,656 | 10/1991 | Howard . |
| 5,069,220 | 12/1991 | Casparie et al. . |
| 5,117,674 | 6/1992 | Howard . |
| 5,178,155 | 1/1993 | Mault . |
| 5,285,794 | 2/1994 | Lynch . |
| 5,299,579 | 4/1994 | Gedeon et al. . |
| 5,402,796 | 4/1995 | Packer et al. . |
| 5,595,181 | 1/1997 | Hubbard . |

FOREIGN PATENT DOCUMENTS

WO 98/12963   4/1998 (WO) .

OTHER PUBLICATIONS

Cane, Roy D., et al., Unreliability of oxygen tension–based indices in reflecting intrapulmonary shunting in critically ill patients, Critical Care Medicine (1988) 16(12): 1243–45.

Capek, J.M., Noninvasive Measurement of Cardiac Output Using Partial $CO_2$ Rebreathing [Dissertation], Rensselaer Polytechnic Institute (1988) 28:351 p. (due to large number of pages, only table of contents and abstract have been copied).

Capek, J.M., et al., Noninvasive Measurement of Cardiac Output Using Partial $CO_2$ Rebreathing, IEEE Trans. Biomed. Eng. (1988) 35(9):653–61.

Cruz, J. C., et al., Understanding the Meaning of the Shunt Fraction Calculation, Journal of Clinical Monitoring (1987) 3(2): 124–34.

(List continued on next page.)

*Primary Examiner*—Eric F. Winakur
*Assistant Examiner*—Navin Natnithithadha
(74) *Attorney, Agent, or Firm*—TraskBritt

(57) ABSTRACT

A method of non-invasively estimating the intrapulmonary shunt in a patient. The method includes non-invasively measuring respiratory flow, respiratory carbon dioxide content, and arterial blood oxygen content. A re-breathing process is employed to facilitate an estimate of the patient's pulmonary capillary blood flow. Any inaccuracies of the arterial blood oxygen content are corrected to provide a substantially accurate arterial blood oxygen content measurement. The respiratory flow, carbon dioxide content and arterial blood oxygen content measurements, and the pulmonary capillary blood flow estimate are employed to estimate an intrapulmonary shunt of the patient. The invention also includes a method of determining the total cardiac output of the patient which considers the estimated intrapulmonary shunt.

43 Claims, 7 Drawing Sheets

OTHER PUBLICATIONS

Davies, Gerald G., et al., Continuous Fick cardiac output compared to thermodilution cardiac output, Critical Care Medicine (1986) 14(10):881–85.

Dean, J. Michael, et al., Arterial blood gas derived variables as estimates of intrapulmonary shunt in critically ill children, Critical Care Medicine (1985) 13(12): 1029–33.

Elliott, C. Gregory, et al., Complications of Pulmonary Artery Catheterization in the Care of Critically Ill Patients, Chest (1979) 76:6, 647–52.

Fick, A., Über die Messung des Blutquantums in den Herzventrikeln, Sitzungsbericht der Physikalisch–Medizinischen Gesellschaft zu Würzburg (1870) 36 (2 pages). of a letter summarizing the article.

Gama de Abreu, Marcelo, et al., Measurement of Pulmonary Capillary Blood Flow for Trending Mixed Venous Blood Oxygen Saturation and Oxygen Delivery, Crit. Care Med. (1998), vol. 26, No. 1 (Suppl.), A106, Abstract #238 (1 page).

Gama de Abreu, Marcelo, et al., Is the Partial $CO_2$ Rebreathing Technique a Useful Tool for Trending Pulmonary Capillary Blood Flow During Adjustments of Peep?, Crit. Care Med. (1998) vol. 26, No. 1 (Suppl.), A106, Abstract #237, (1 page).

Gama de Abreu, et al., Partial carbon dioxide rebreathing: A reliable technique for noninvasive measurement of non-shunted pulmonary capillary blood flow, Crit. Care Med. (1997) 25(4):675–83.

Gedeon, A., et al., Noninvasive Cardiac Output Determined with a New Method Based on Gas Exchange Measurements and Carbon Dioxide Rebreathing: A Study in Animals/Pigs, J. Clin. Monit. (1992) 8(4):267–78.

Gedeon, A., et al., A new method for noninvasive bedside determination of pulmonary blood flow, Med. & Biol. Eng. & Comput. (1980) 18:411–418.

Guyton, A.E., et al., Measurement of cardiac output by the direct Fick method, In: Cardiac output and its regulation, W.B. Saunders Company (1973) 21–39.

Hope, D.A., et al., Non–invasive estimation of venous admixture: validation of a new formula, British Journal of Anaesthesia (1995) 74:538–43.

Kyoku, I., et al., Measurement of cardiac output by Fick method using $CO_2$ analyzer Servo, Kyobu Geka. Japanese Journal of Thoracic Surgery (1988) 41(12):966–70.

Lobdell, Donn D., An invertible simple equation for computation of blood $O_2$ dissociation relations, American Physiological Society: (1981) 971–73. Including English translation. (5 pages).

Lynch, J., et al., Comparison of a modified Fick method with thermodilution for determining cardiac output in critically ill patients on mechanical ventilation, Intensive Care Med. (1990) 16:248–51.

Mahutte, C. Kees, et al., Relationship of Thermodilution Cardiac Output to Metabolic Measurements and Mixed Venous Oxygen Saturation, Chest (1993) 104(4):1236–42.

Miller, D.M., et al., A Simple Method for the Continuous Noninvasive Estimate of Cardiac Output Using the Maxima Breathing System. A Pilot Study, Anaesth. Intens. Care (1997) 25(1):23–28.

Österlund, B., et al., A new method of using gas exchange measurements for the noninvasive determination of cardiac output: clinical experiences in adults following cardiac surgery, Acta Anaesthesiol Scand (1995) 39:727–32.

Sackner, Marvin A., Measurement of cardiac output by alveolar gas exchange, Handbook of Physiology – The Respiratory System IV, Chapter 13, 233–55.

Sapsford, D. J., et al., The $PIO_2$ vs. $SpO_2$ diagram: a non–invasive measure of pulmonary oxygen exchange, European Journal of Anaesthesiology (1995) 12: 375–86.

Serveringhaus, John W., Simple, accurate equations for human blood $O_2$ dissociation computations, American Physiological Society: (1979) 599–602.

Shepherd, A. P., et al., Role of Oximeter Error in the Diagnosis of Shunts, Cath. and Cardio. Diagnosis (1996) 37:435–46.

Spalding, H. K., et al., Carbon Dioxide ($CO_2$) Elimination Rate Accurately Predicts Cardiac Output, Anesthesiology (1997) 87(3A) (1 page).

Sprung, Charles L., et al., Ventricular Arrhythmias During Swan–Ganz Catheterization of the Critically Ill, Chest (1981) 79:4, 413–15.

Taskar, V., et al., Dynamics of Carbon Dioxide Elimination Following Ventilator Resetting, Chest (1995) 108:1, 196–202.

Winkler, Tilo, et al., Pulmonary Capillary Blood Flow by Partial $CO_2$ Rebreathing: A Simulation Study Using a Bicompartmental Model of Gas Exchange, Crit. Care Med. (1998), vol. 26, No. 1 (Suppl.), A105, Abstract #234, (1 page).

H. Blomquist et al., A Non–Invasive Technique for Measurement of Lung Perfusion, Intensive Care Medicine 1986; 12:172.

R.J. Bosman et al, Non–Invasive Pulimonary Blood Flow Measurement by Means of $CO_2$ Analysis Of Expiratory Gases, Intensive Care Medicine 1991, 17:98–102.

A. Gedeon, Non–Invasive Pulmonary Blood Flow for Optimal Peep, ICOR AB, Ulvsundavagen 178 B, S–161 30 Bromma, Sweden, pp. 49–58.

$n := 1.58678$
$a := 0.34332$
$b := 0.64073$
$c := 0.34128$ $S := 0, 0.001 .. 0.999$ $$x(S) := \left[ \frac{a \cdot S \cdot c - \sqrt{(a \cdot S \cdot c)^2 - 4 \cdot S \cdot (S-1) \cdot b}}{2 \cdot b \cdot (S-1)} \right]^{\frac{1}{n}} \cdot 26.8$$

$x(0.85) = 50.232$    $x(0.99) = 128.386$
$x(0.90) = 58.769$    $x(0.999) = 263.846$
$x(0.95) = 75.338$    $x(0.9999) = 517.714$
                     $x(0.99999) = 905.512$

METHODS OF NON-INVASIVELY ESTIMATING INTRAPULMONARY SHUNT FRACTION AND MEASURING CARDIAC OUTPUT

CROSS REFERENCE TO RELATED APPLICATION

This application is a divisional of application Ser. No. 09/150,450, filed Sep. 9, 1998, now U.S. Pat. No. 6,042,550.

BACKGROUND OF THE INVENTION

1. Field of the Invention

The present invention relates to a method of non-invasively measuring the cardiac output of a patient. Particularly, the present invention relates to a method of measuring cardiac output which accounts for the amount of intrapulmonary shunted blood. More particularly, the present invention relates to a method of non-invasively estimating intrapulmonary shunt and considering the intrapulmonary shunt with re-breathing pulmonary capillary blood flow measurements in measuring the cardiac output.

2. Background of Related Art

Cardiac output is one of various hemodynamic parameters that may be monitored in critically ill patients. Conventionally, cardiac output has been measured by direct, invasive techniques, such as by thermodilution using a Swan-Ganz catheter. Invasive measurement of cardiac output is undesirable because of the potential for harming the patient that is typically associated with the use of such a catheter.

Thus, non-invasive techniques for determining cardiac output have been developed. Cardiac output is the sum of blood flow through the lungs that participates in gas exchange, which is typically referred to as pulmonary capillary blood flow, and the blood flow that does not participate in gas exchange, which is typically referred to as intrapulmonary shunt flow or venous admixture.

The pulmonary capillary blood flow of a patient has been non-invasively determined by employing various respiratory, blood, and blood gas profile parameters in a derivation of the Fick equation (typically either the $O_2$ Fick equation or the $CO_2$ Fick equation), such as by the use of partial and total re-breathing techniques.

The carbon dioxide Fick equation, which may be employed to determine cardiac output, follows:

$$Q_t = VCO_2/(CvCO_2 - CaCO_2),$$

where $Q_t$ is the cardiac output of the patient, $VCO_2$ is the carbon dioxide elimination of the patient, $CvCO_2$ is the carbon dioxide content of the venous blood of the patient, and $CaCO_2$ is the carbon dioxide content of the arterial blood of the patient.

The carbon dioxide elimination of the patient may be non-invasively measured as the difference per breath between the volume of carbon dioxide inhaled during inspiration and the volume of carbon dioxide exhaled during expiration, and is typically calculated as the integral of the carbon dioxide signal times the rate of flow over an entire breath. The volume of carbon dioxide inhaled and exhaled may each be corrected for any deadspace or for any intrapulmonary shunt.

The partial pressure of end tidal carbon dioxide ($PetCO_2$ or $etCO_2$) is also measured in re-breathing processes. The partial pressure of end-tidal carbon dioxide, after correcting for any deadspace, is typically assumed to be approximately equal to the partial pressure of carbon dioxide in the alveoli ($PACO_2$) of the patient or, if there is no intrapulmonary shunt, the partial pressure of carbon dioxide in the arterial blood of the patient ($PaCO_2$). Conventionally employed Fick methods of determining cardiac output typically include a direct, invasive determination of $CvCO_2$ by analyzing a sample of the patient's mixed venous blood. The re-breathing process is typically employed to either estimate the carbon dioxide content of mixed venous blood (in total re-breathing) or to obviate the need to know the carbon dioxide content of the mixed venous blood (by partial re-breathing) or determine the partial pressure of carbon dioxide in the patient's venous blood ($PVCO_2$).

Re-breathing processes typically include the inhalation of a gas mixture which includes carbon dioxide. During re-breathing, the carbon dioxide elimination typically decreases. In total re-breathing, carbon dioxide elimination decreases to near zero. In partial re-breathing, carbon dioxide elimination does not cease. Thus, in partial re-breathing, the decrease in carbon dioxide elimination is not as large as that of total re-breathing.

Re-breathing can be conducted with a re-breathing circuit, which causes a patient to inhale a gas mixture that includes carbon dioxide. FIG. 1 schematically illustrates an exemplary re-breathing circuit 50 that includes a tubular airway 52 that communicates air flow to and from the lungs of a patient. Tubular airway 52 may be placed in communication with the trachea of the patient by known intubation processes, or by connection to a breathing mask positioned over the nose and/or mouth of the patient. A flow meter 72, such as a pneumotachometer, and a carbon dioxide sensor 74, which is typically referred to as a capnometer, are disposed between tubular airway 52 and a length of hose 60, and are exposed to any air that flows through re-breathing circuit 50. Both ends of another length of hose, which is referred to as deadspace 70, communicate with hose 60. The two ends of deadspace 70 are separated from one another by a two-way valve 68, which may be positioned to direct the flow of air through deadspace 70. Deadspace 70 may also include an expandable section 62. A Y-piece 58, disposed on hose 60 opposite flow meter 72 and carbon dioxide sensor 74, facilitates the connection of an inspiratory hose 54 and an expiratory hose 56 to re-breathing circuit 50 and the flow communication of the inspiratory hose 54 and expiratory hose 56 with hose 60. During inhalation, gas flows into inspiratory hose 54 from the atmosphere or a ventilator (not shown). During normal breathing, valve 68 is positioned to prevent inhaled and exhaled air from flowing through deadspace 70. During re-breathing, valve 68 is positioned to direct the flow of exhaled and inhaled gases through deadspace 70.

During total re-breathing, the partial pressure of end-tidal carbon dioxide is typically assumed to be equal to the partial pressure of carbon dioxide in the venous blood ($PvCO_2$) of the patient, as well as to the partial pressure of carbon dioxide in the arterial blood ($PaCO_2$) of the patient and to the partial pressure of carbon dioxide in the alveolar blood ($PACO_2$) of the patient. The partial pressure of carbon dioxide in blood may be converted to the content of carbon dioxide in blood by means of a carbon dioxide dissociation curve.

In partial re-breathing, measurements during normal breathing and subsequent re-breathing are substituted into the carbon dioxide Fick equation. This results in a system of two equations and two unknowns (carbon dioxide content in the mixed venous blood and cardiac output), from which pulmonary capillary blood flow can be determined without knowing the carbon dioxide content of the mixed venous blood.

Known re-breathing techniques for non-invasively determining cardiac output are, however, somewhat undesirable since they typically measure pulmonary capillary blood flow and do not account for intrapulmonary shunt flow.

The failure of conventional non-invasive re-breathing techniques for determining cardiac output to account for intrapulmonary shunt was recognized, and techniques were developed to estimate the intrapulmonary shunt. Some intrapulmonary shunt flow ($Q_s$) or shunt fraction ($Q_s/Q_t$) or venous admixture estimates employ values obtained from pulse oximetry ($SpO_2$) and inspiratory oxygen fractions ($FiO_2$). In B. Österlund et al., A new method of using gas exchange measurements for the noninvasive determination of cardiac output: clinical experiences in adults following cardiac surgery, Acta Anaesthesiol. Scand. (1995) 39:727–732 ("Österlund"), Österlund notes that while pulse oximetry measurements provide accurate shunt estimates when $FiO_2$ is close to 0.21 (approximately the fraction of oxygen in the air), when the fraction of inspired oxygen ($FiO_2$) exceeds 0.5, as it typically does when a patient is artificially ventilated, the arterial oxygen tension of a patient should be measured directly (i.e., invasively). Moreover, as FIG. 2 illustrates, as the blood becomes about 95–100% saturated with oxygen, due to the steepness of the oxygen tension-saturation curve of FIG. 2, precise and accurate arterial blood oxygen saturation measurements ($SaO_2$) are necessary to accurately determine the partial pressure of oxygen in a patient's arterial blood. Thus, since pulmonary capillary blood flow measurements are often taken while a patient's breathing is artificially ventilated, and since $FiO_2$ is typically greater than about 0.5, the technique disclosed in Österlund often undesirably requires invasive measurement of $SaO_2$.

Accordingly, there is a need for a method of non-invasively and accurately estimating intrapulmonary shunt, as well as a method of accounting for the estimated intrapulmonary shunt in determining the cardiac output of a patient by re-breathing techniques.

SUMMARY OF THE INVENTION

The methods of the present invention address each of the foregoing needs.

The present invention includes a method of non-invasively estimating the intrapulmonary shunt, pulmonary capillary blood flow and cardiac output of a patient. The shunt-estimating method according to the present invention includes non-invasively measuring the pulmonary capillary blood flow of the patient, measuring a volume of carbon dioxide exhaled by the patient, determining the difference between the end capillary oxygen content and the arterial oxygen content of the patient's blood, dividing the difference by the volume of carbon dioxide exhaled by the patient, and multiplying the difference by the patient's pulmonary capillary blood flow and by the patient's respiratory quotient (RQ). The respiratory quotient is the volume of carbon dioxide exhaled by the patient divided by the volume of oxygen exhaled by the patient. The respiratory quotient may be an assumed value (e.g., RQ=0.86).

The pulmonary capillary blood flow of the patient may be determined by known techniques, such as partial or total re-breathing techniques.

The patient's cardiac output ($Q_t$) includes a portion, which is typically identified as pulmonary capillary blood flow $Q_{pcbf}$, that flows through pulmonary capillaries 164 (FIG. 5) and participates in gas exchange in the lungs 150, and a portion that does not participate in blood gas exchange, which is referred to as the intrapulmonary shunt 165, venous admixture, shunted blood, or simply as "shunt". The corrected cardiac output may be determined by adding the non-invasively measured volume rate of pulmonary capillary blood flow ($Q_{pcbf}$) and the volume rate of flow of the intrapulmonary shunt flow of the patient ($Q_s$) by the following equation:

$$Q_t = Q_{pcbf} + Q_s.$$

Alternatively, a patient's corrected cardiac output may be determined as follows:

$$Q_t = Q_{pcbf}/(1 - Q_s/Q_t),$$

where $Q_s/Q_t$ is the intrapulmonary shunt fraction.

The uncorrected volume/rate of the patient's pulmonary capillary blood flow ($Q_{pcbf}$) is preferably measured by non-invasive techniques, such as known partial or total re-breathing techniques, and may be employed with a variety of carbon dioxide, respiratory flow and pulse oximetry apparatus.

The shunt fraction of the patient's pulmonary capillary blood flow may be derived from various respiratory profile parameters, many of which may also be measured by non-invasive techniques. $Q_s/Q_t$ may be estimated in accordance with the following equation:

$$Q_s/Q_t = \frac{Cc'O_2 - CaO_2}{Cc'O_2 - CvO_2},$$

where $Cc'O_2$ is the end-capillary oxygen content, $CaO_2$ is the arterial oxygen content, and $CvO_2$ is the mixed venous oxygen content. The denominator of the preceding formula ($Cc'O_2 - CvO_2$) can be derived from the Fick oxygen equation that is typically employed in known re-breathing techniques for determining pulmonary capillary blood flow:

$$Cc'O_2 - CvO_2 = VO_2/Q_{pcbf}$$

Since the respiratory quotient is the ratio of the carbon dioxide elimination ($VCO_2$) to the amount of oxygen consumed ($VO_2$) by the patient, as defined by the following equation:

$$RQ = VCO_2/VO_2,$$

$VCO_2/RQ$ may be substituted for $VO_2$. Such substitution of $VCO_2/RQ$ for $VO_2$ is preferred because it is difficult to accurately measure $VO_2$, especially in patients who require an elevated fraction of inspired oxygen. Moreover, RQ can be assumed with accuracy (typically about 0.7 to 1.0, and more particularly about 0.8 to 0.9 or 0.86). Thus, $$Cc'O_2 - CvO_2 = VCO_2/(Q_{pcbf} RQ).$$

Accordingly, the shunt fraction, $Q_s/Q_t$, may be estimated by the following formula:

$$Q_s/Q_t = \frac{\frac{Cc'O_2 - CaO_2}{V_{CO_2}}}{Q_{pcbf} \cdot RQ}.$$

The $VCO_2$ measurement is preferably based on the alveolar $CO_2$ output of the patient, and may be measured by known re-breathing techniques.

The end-capillary oxygen content, $Cc'O_2$, may be calculated by the following equation:

$$Cc'O_2 = (P_AO_2 \cdot \alpha) + (Sc'O_2 \cdot Hb_{capacity} \cdot Hb_{conc}),$$

where the alveolar oxygen tension of the patient may be calculated by the following formula:

$$PAO_2 = (FiO_2 \cdot (P_{bar} - P_{H2O})) - (PaCO_2/RQ \cdot (1 - (FiO_2 \cdot (1-RQ)))),$$

where $P_{bar}$ is the barometric pressure, $P_{H2O}$ is the saturated water vapor pressure of a sample at ambient temperature and $PaCO_2$ is the partial pressure of $CO_2$ in the patient's arterial blood, which may be assumed, calculated as known in the art from non-invasively obtained arterial blood gas data, or obtained by direct measurement. The blood oxygen solubility coefficient ($\alpha$), the end-capillary blood saturation ($Sc'O_2$), hemoglobin concentration ($Hb_{conc}$), and hemoglobin capacity ($Hb_{capacity}$) values may each be assumed values or determined by known techniques.

The arterial oxygen content, $CaO_2$, may be calculated by the following equation:

$$CaO_2 = (PaO_2 \cdot \alpha) + (SaO_2 \cdot Hb_{capacity} \cdot Hb_{conc}).$$

Since $PaO_2$ is a function of $SaO_2$, which may be approximated by $SpO_2$, the partial pressure of the patient's arterial oxygen, $PaO_2$, may be calculated from the oxygen saturation ($SaO_2$) of the patient's arterial blood using an invertible version of the blood oxygen tension-saturation relationship, as represented by the Lobdell equation. Lobdell, D. D., An invertible simple equation for computation of blood $O_2$ dissociation relations, *J. Appl. Physiol.* (1981) 971–973.

Arterial blood oxygen saturation, $SaO_2$, may be determined by known pulse oximetry ($SpO_2$) techniques. Pulse oximetry techniques may provide somewhat inaccurate blood oxygen saturation data (i.e., $SaO_2$ values). As the inverted tension-saturation curve is relatively steep at about 95–100% blood oxygen saturation, it is, therefore, difficult to accurately derive $PaO_2$ from $SaO_2$. Thus, the $SpO_2$ measurement is corrected to provide a more accurate $PaO_2$ value.

Alternatively, the measured $SaO_2$ or $PaO_2$ and $FiO_2$ of the patient may be employed with an iso-shunt diagram or one or more equations that may be employed to generate an iso-shunt diagram to non-invasively estimate the intrapulmonary shunt fraction of the cardiac output of a patient.

Once a non-invasive determination of a patient's pulmonary capillary blood flow has been made and the intrapulmonary shunt flow or shunt fraction of the patient estimated, the patient's cardiac output ($Q_t$) may be determined.

The advantages of the present invention will become apparent to those of skill in the art through a consideration of the ensuing description, the accompanying drawings, and the appended claims.

DETAILED DESCRIPTION OF THE INVENTION

The present invention includes a method of estimating the flow or fraction of blood that does not participate in the exchange of oxygen ($O_2$) and carbon dioxide ($CO_2$) in the pulmonary capillaries, which is referred to as "intrapulmonary shunt", "venous admixture", "shunted blood", or simply as "shunt". The present invention also includes a method of calculating cardiac output based on the shunt estimate.

Due to the difficulty of measuring the amount of oxygen consumed by a patient ($VO_2$), especially in patients who require an elevated fraction of inspired oxygen, pulmonary capillary blood flow ($Q_{pcbf}$) cardiac output (CO), and the estimated shunt fraction are preferably measured in terms of the amount of carbon dioxide excreted into the lungs of the patient, which is typically measured in terms of carbon dioxide elimination ($VCO_2$). The Fick equation for measurement of cardiac output, in terms of $CO_2$, is:

$$Q_t = VCO_2/(CvCO_2 - CaCO_2).$$

Measuring Respiratory, Blood and Blood Gas Profile Parameters

Figure 1:
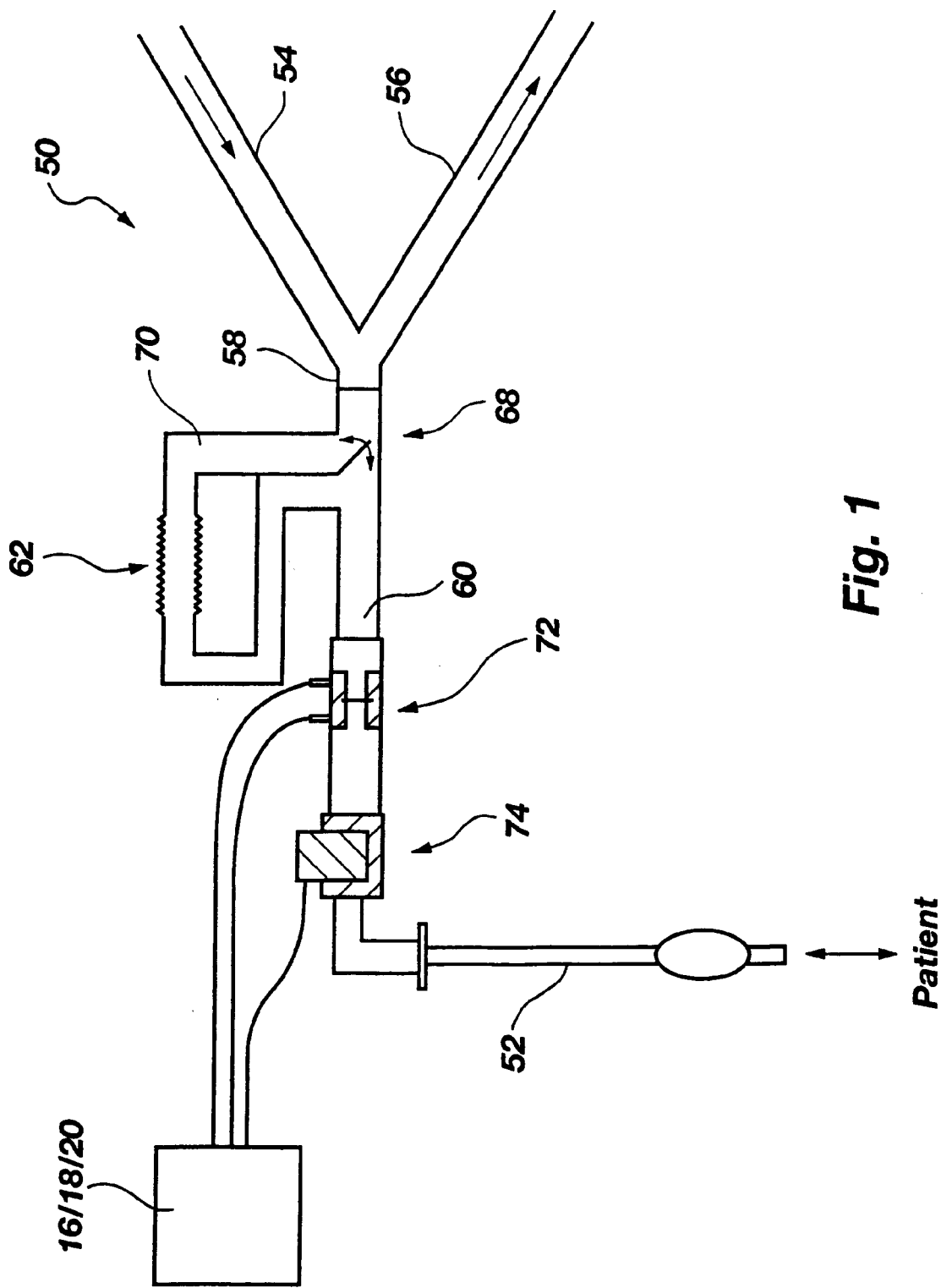
FIG. 1 is a schematic representation of an exemplary re-breathing circuit that may be employed with the methods of the present invention.
Figure 2:
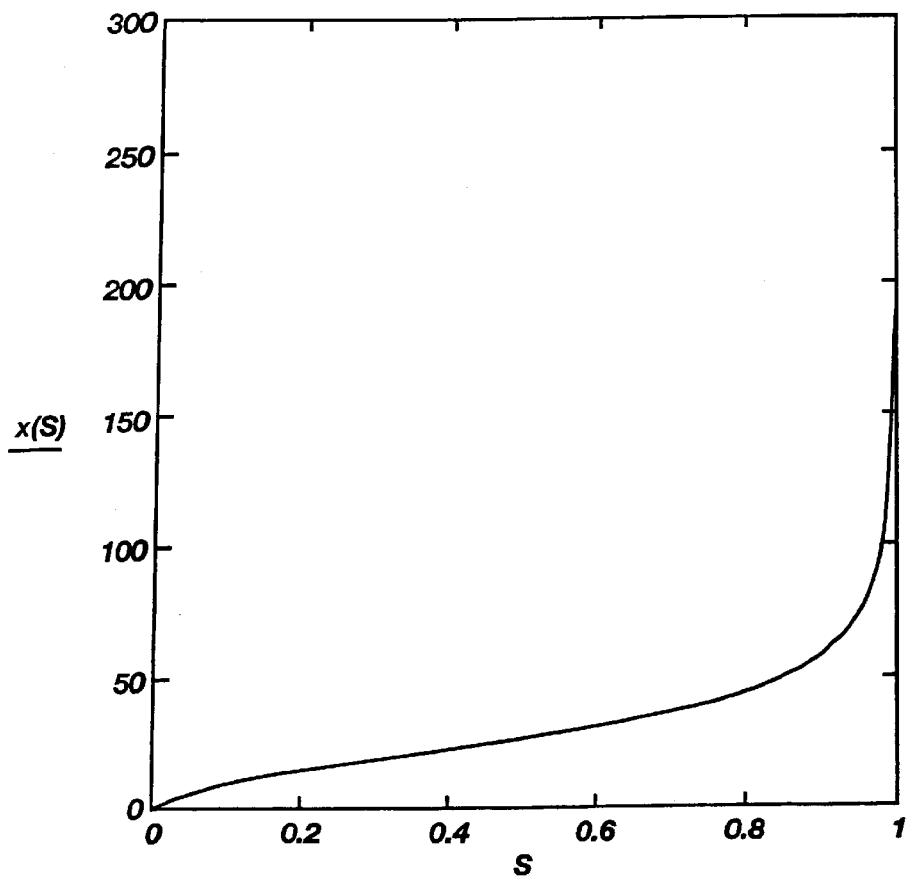
FIG. 2 is a line graph of an inverse Lobdell relation, which illustrates the relatively large difference in $PaO_2$ values derived from relatively close $SpO_2$ values—in the 95–100% range—and, thus, the potential for error when inaccurate $SPO_2$ measurements are made.
Figure 3:
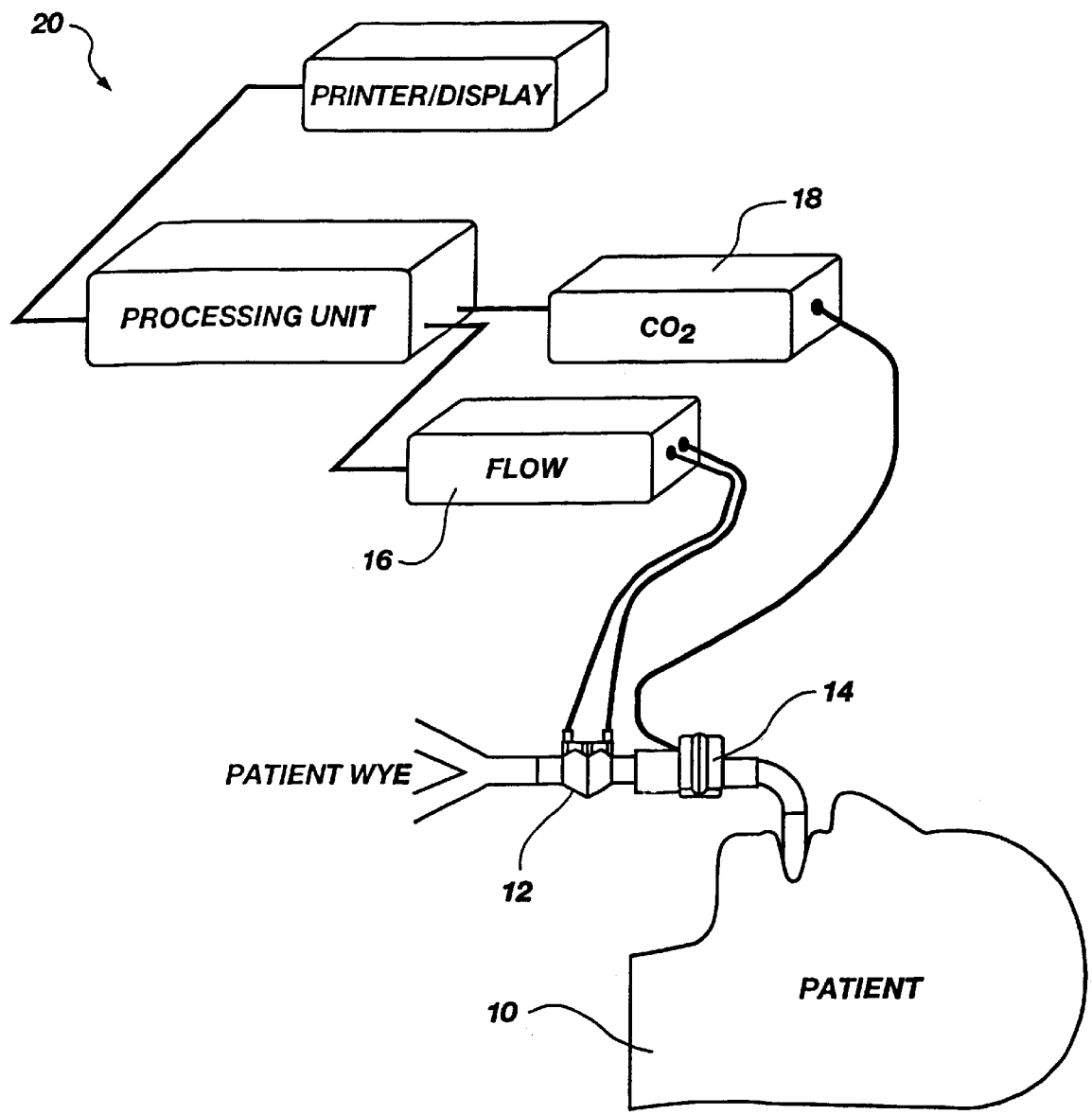
FIG. 3 is a schematic representation which illustrates the various componentry that may be utilized to measure respiratory profile parameters that are employed in the methods of the present invention.
Figure 6:
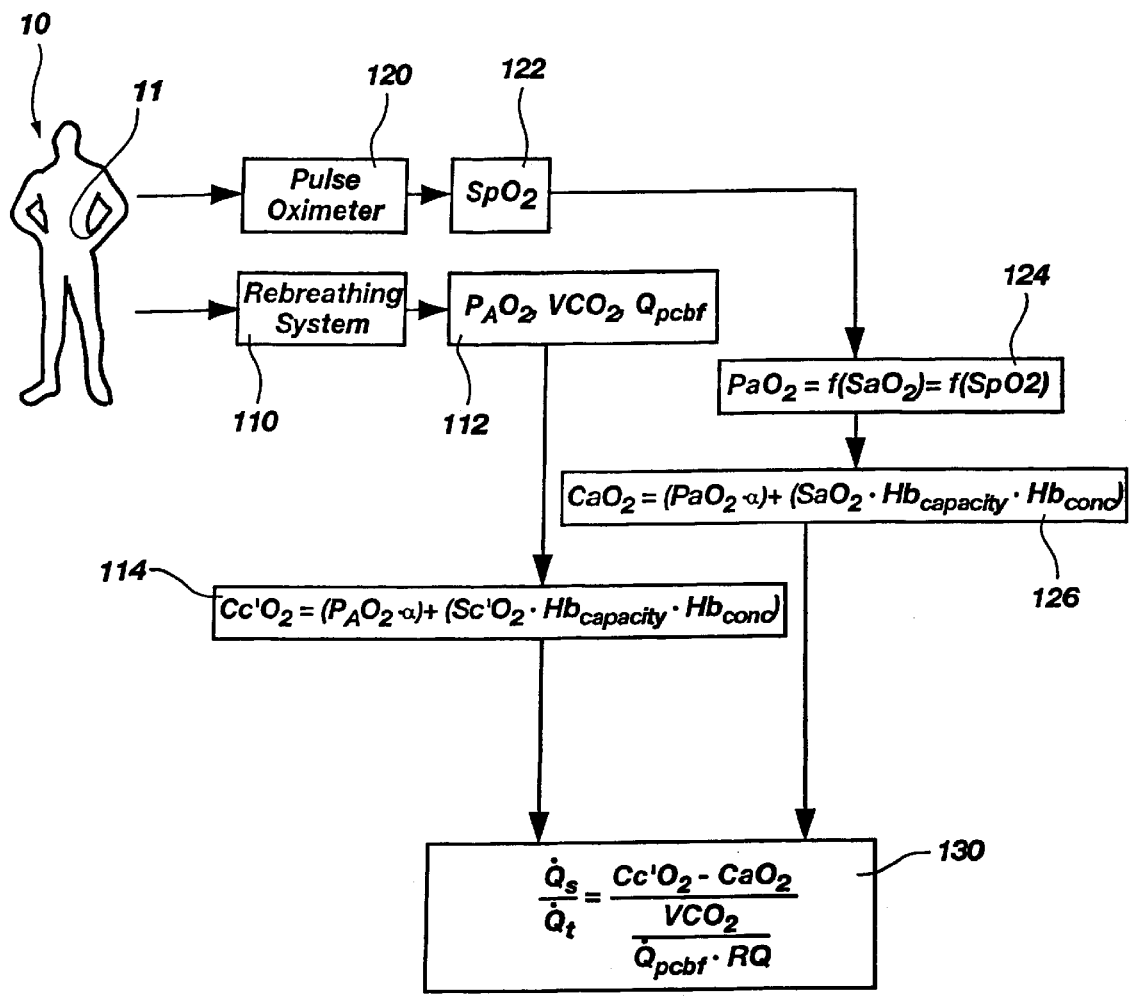
FIG. 6 is a flow diagram of a preferred embodiment of the method of the present invention.

With reference to FIG. 6, calculating pulmonary capillary blood flow in accordance with the method of the present invention includes measuring the flow rates and $CO_2$ fraction of gas mixtures that are inhaled and exhaled by a patient 10 over the course of the patient's breathing, at 110. With reference to FIG. 3, a flow sensor 12 of a known type, such as the differential-pressure type respiratory flow sensors manufactured by Novametrix Medical Systems Inc. ("Novametrix") of Wallingford, Conn. (e.g, the Pediatric/Adult Flow Sensor (Catalog No. 6717) or the Neonatal Flow Sensor (Catalog No. 6718)), which may be operatively attached to a ventilation apparatus (not shown), as well as respiratory flow sensors based on other operating principles and manufactured and marketed by others, may be employed to measure the flow rates of the breathing of patient 10. A $CO_2$ sensor 14, such as the CAPNOSTAT® $CO_2$ sensor and a complementary airway adapter (e.g., the Pediatric/Adult Single Patient Use Airway Adapter (Catalog No. 6063), the Pediatric/Adult Reusable Airway Adapter (Catalog No. 7007), or the Neonatal/Pediatric Reusable Airway Adapter (Catalog No. 7053)), which are manufactured by Novametrix, as well as mainstream or sidestream $CO_2$ sensors manufactured or marketed by others, may be employed to measure the $CO_2$ fraction of gas mixtures that is inhaled and exhaled by patient 10. Flow sensor 12 and $CO_2$ sensor 14 are connected to a flow monitor 16 and a $CO_2$ monitor 18, respectively, each of which may be operatively associated with a computer 20 so that data from the flow and $CO_2$ monitors 16 and 18 representative of the signals from each of flow sensor 12 and $CO_2$ sensor 14 may be detected by computer 20 and processed according to programming (e.g., by software) thereof Preferably, raw flow and $CO_2$ signals from the flow monitor and $CO_2$ sensor are filtered, as known in the art, to remove any significant artifacts. As respiratory flow and $CO_2$ pressure measurements are made, the respiratory flow and $CO_2$ pressure data may be stored by computer 20. Thus, pulmonary capillary blood flow may be calculated, in accordance with the foregoing equation or by any other equation known in the art, by computer 20.

Each breath, or breathing cycle, of patient 10 may be delineated as known in the art, such as by continually monitoring the flow rate of the breathing of patient 10.

Figure 4:
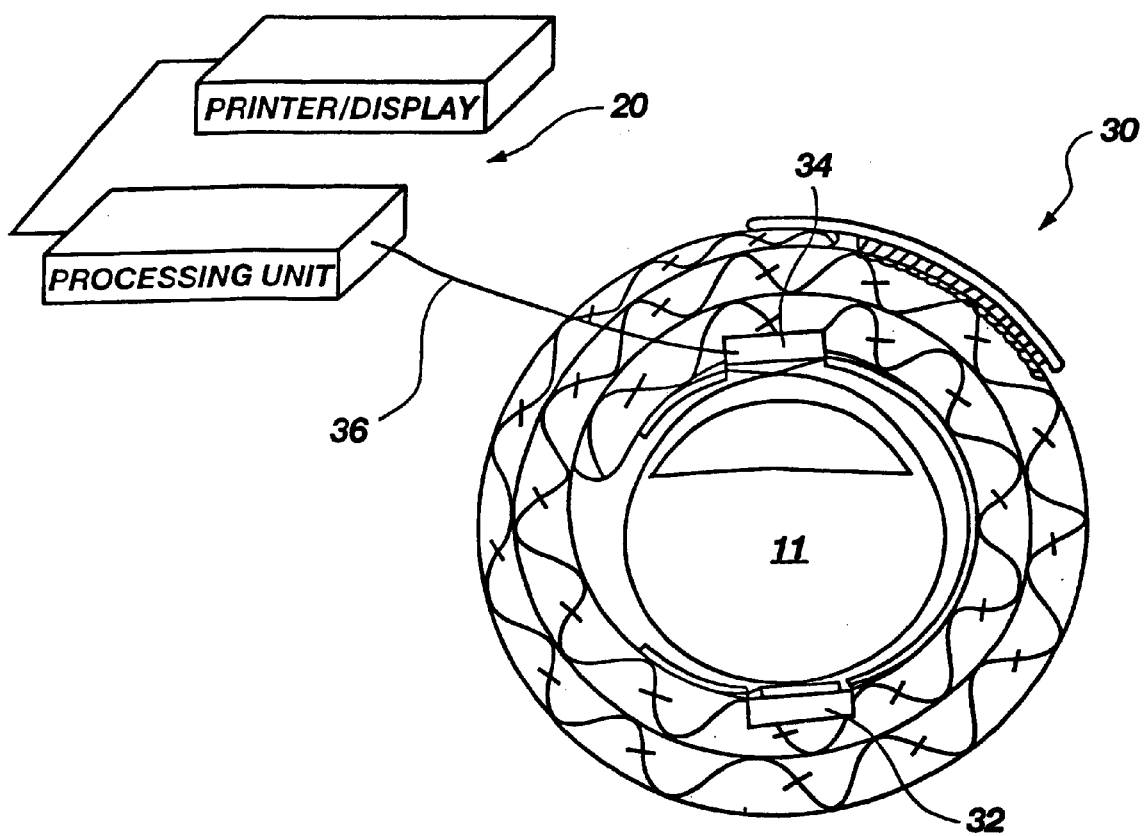
FIG. 4 is a schematic representation which illustrates a pulse oximetry sensor and associated monitor, which may be employed in association with the methods of the present invention.

Referring now to FIG. 4, at 120 of the flow diagram of FIG. 6, blood oxygen measurements may be made, at 122 of FIG. 6, by non-invasive means, such as by a pulse oximetry sensor 30 of a type known in the art, such as the OXYSNAP™ or Y-SENSOR™, both of which are manufactured by Novametrix. Pulse oximetry sensor 30 includes a light emitting diode (LED) assembly 32 and a photodiode 34 which are positionable on opposite sides of an appendage of the body of a patient, such as a finger 11, hand, toe, heel, foot, ear lobe, nose, or tongue. $SpO_2$ signals, which may be conveyed from pulse oximetry sensor 30 to computer 20, as known in the art, such as by a cable connector 36, are subsequently employed in the methods of the present invention.

Various other values that are employed in the methods of the present invention may be measured separately or assumed, then used in the methods, such as by entering these values into computer 20.

Preliminarily Determining Pulmonary Capillary Blood Flow

Referring again to the flow diagram of FIG. 6, at 112, for each breathing cycle, the partial pressure of end-tidal $CO_2$, carbon dioxide elimination ($VCO_2$), the fraction of inspired, or "mixed inspired", $CO_2$, and the airway deadspace are calculated. End-tidal $CO_2$ is measured as known in the art. Carbon dioxide elimination is typically calculated as the integral of the respiratory flow over a breathing cycle (in milliliters) multiplied by the fraction of $CO_2$ over the entire breath. The fraction of inspired $CO_2$ is the integral of $CO_2$ fraction times the air flow during inspiration, divided by the volume (in milliliters) of inspired gas.

The values of $VCO_2$ and $PetCO_2$ may be filtered by employing a three-point median filter, which uses a median value from the most recent value of recorded $VCO_2$ and $PetCO_2$ values and the two values that precede the most recent measured value, as known in the art.

Figure 5:
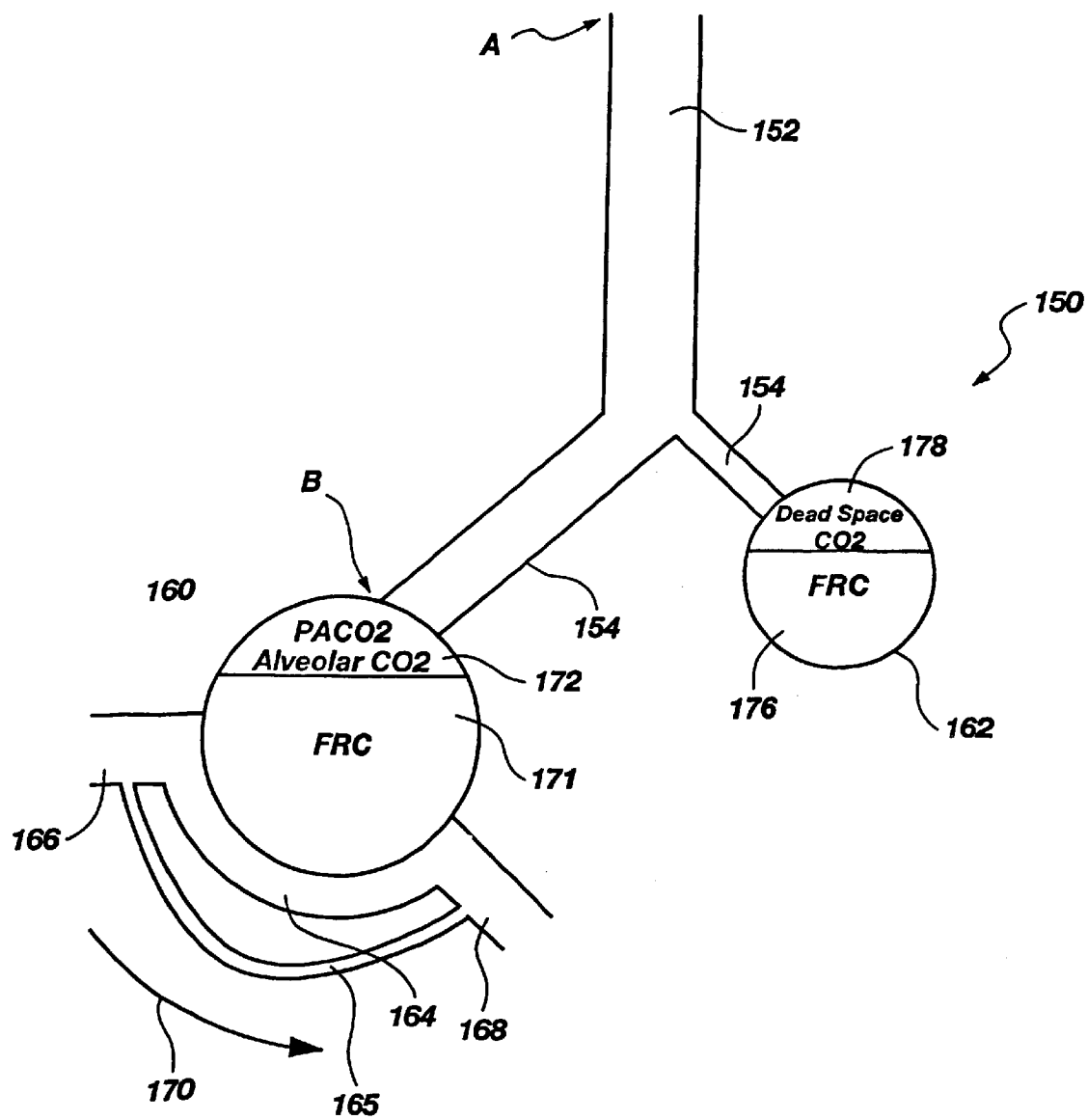
FIG. 5 is a schematic representation of the lungs of a patient.

Preferably, when calculating $VCO_2$, the $VCO_2$ value is corrected to account for anatomic deadspace and alveolar deadspace. With reference to FIG. 5, the lungs 150 of a patient may be described as including a trachea 152, two bronchi 154 and numerous alveoli 160, 162. The anatomic, or "serial", deadspace of lungs 150 includes the volume of the trachea 152, bronchi 154, and other components of lungs 150 which hold gases, but do not participate in gas exchange. The anatomic deadspace exists approximately in the region located between arrows A and B. The so-called "shunted" blood bypasses pulmonary capillaries by way of an intrapulmonary shunt 165.

Lungs 150 typically include alveoli 160 that are in contact with blood flow and which can facilitate oxygenation of the blood, which are referred to as "perfused" alveoli, as well as unperfused alveoli 162. Both perfused alveoli 160 and unperfused alveoli 162 may be ventilated. The volume of unperfused alveoli is the alveolar deadspace.

Perfused alveoli 160 are surrounded by and in contact with pulmonary capillaries 164. As deoxygenated blood 166 enters pulmonary capillaries 164, oxygen binds to the hemoglobin molecules of the red blood cells of the blood and $CO_2$ is released from the hemoglobin. Blood that exits pulmonary capillaries 164 in the direction of arrow 170 is referred to as oxygenated blood 168. In alveoli 160 and 162, a volume of gas known as the functional residual capacity (FRC) 171 remains following exhalation. The alveolar $CO_2$ is expired from a portion 172 of each of the alveoli 160 that is evacuated, or ventilated, during exhalation.

The ventilated portion 178 of each of the unperfused alveoli 162 may also include $CO_2$. The $CO_2$ of ventilated portion 178 of each of the unperfused alveoli 162, however, is not the result of $O_2$ and $CO_2$ exchange in that alveolus. Since the ventilated portion 178 of each of the unperfused alveoli 162 is ventilated in parallel with the perfused alveoli, ventilated portion 178 is typically referred to as "parallel" deadspace (PDS). Unperfused alveoli 162 also include a FRC 176, which includes a volume of gas that is not evacuated during a breath.

In calculating the partial pressure of $CO_2$ in the alveoli ($PACO_2$) of the patient, the FRC and the partial pressure of $CO_2$ in the parallel deadspace in each of the unperfused alveoli 162 is preferably accounted for. FRC may be estimated as a function of body weight and the airway deadspace volume by the following equation:

$$FRC = FRC\text{-}factor \cdot (airway\ deadspace + offset\ value),$$

where FRC-factor is either an experimentally determined value or is based on published data (e.g., "experiential" data) known in the art, and the offset value is a fixed constant which compensates for breathing masks or other equipment components that may add deadspace to the breathing circuit and thereby unacceptably skew the relationship between FRC and deadspace.

The partial pressure of $CO_2$ in the parallel deadspace ($CO_{2_{PDS}}$) may be calculated from the mixed inspired $CO_2$ ($Vi_{CO2}$) added to the product of the serial deadspace multiplied by the end tidal $CO_2$ of the previous breath ($PerCO_2$ (n−1)). Because the average partial pressure of $CO_2$ in the parallel deadspace is equal to the partial pressure of $CO_2$ in the parallel deadspace divided by the tidal volume ($V_t$) (i.e., the total volume of one respiratory cycle, or breath), the partial pressure of $CO_2$ in the parallel deadspace may be calculated on a breath-by-breath basis, as follows:

$$PCO_{2\,PDS}(n) = [FRC/(FRC+V_t)] \cdot PCO_{2\,PDS}(n-1) + (P_{bar} \cdot (([Vi_{CO2} + deadspace \cdot (PetCO_2(n-1)/P_{bar})]/V_t) \cdot [V_t/(V_t+FRC)])),$$

where (n) indicates a respiratory profile parameter (in this case, the partial pressure of $CO_2$ in the parallel deadspace) from the most recent breath and (n−1) indicates a respiratory profile parameter from the previous breath.

The partial pressure of end-tidal $CO_2$, which is assumed to be substantially equal to a weighted average of the partial pressure of $CO_2$ in all of the perfused and unperfused alveoli of a patient, may then be calculated as follows:

$$PetCO_2 = \textcircled{r} \cdot PACO_2) + (1-r)PCO_{2\,PDS},$$

where r is the perfusion ratio, which is calculated as the ratio of perfused alveolar ventilation to the total alveolar ventilation, or $(V_A - V_{PDS})/V_A$. The perfusion ratio may be assumed to be about 0.95 or estimated as known in the art.

By rearranging the previous equation, the alveolar $CO_2$ partial pressure of the patient may be calculated. Preferably, alveolar $CO_2$ partial pressure is calculated from the end-tidal $CO_2$ and the $CO_2$ in the parallel deadspace, as follows:

$$PACO_2 = [PetCO_2 - (1-r)PCO_{2PDS}]/r.$$

The alveolar $CO_2$ partial pressure may then be converted to alveolar blood $CO_2$ content ($CACO_2$) using an equation, such as the following:

$$CACO_2 = (6.957 \cdot Hb_{conc} - 94.864) \cdot 1n(1+0.1933 \, (PACO_2)),$$

where $CACO_2$ is the content of $CO_2$ in the alveolar blood and Hb is the concentration of hemoglobin in the blood of the pulmonary capillaries. J. M. Capek and R. J. Roy, *IEEE Transactions on Biomedical Engineering* (1988) 35(9) :653–661. In some instances, a hemoglobin count and, therefore, the hemoglobin concentration are available and may be employed in calculating the $CO_2$ content. If a hemoglobin count or concentration is not available, another value that is based upon experiential or otherwise known data (e.g., 11.0 g/dl) may be employed in calculating the alveolar $CO_2$ content.

In calculating $VCO_2$, the FRC and alveolar deadspace of the lungs of a patient may be accounted for by multiplying the FRC by the change in end tidal partial pressure, such as by the following equation:

$$VCO_{2\,corrected} = VCO_2 + FRC \times \Delta PetCO_2/P_{bar},$$

where $\Delta PetCO_2$ is the breath-to-breath change in $PetCO_2$.

Baseline $PetCO_2$ and $VCO_2$ values, which are also referred to as "before re-breathing $PetCO_2$" and "before re-breathing $VCO_2$", respectively, occur during normal breathing and may be calculated as the average of a group of samples taken before the re-breathing process (e.g., the average of all samples between about 27 and 0 seconds before the start of a known re-breathing process). A $VCO_2$ value, which is typically referred to as "during re-breathing $VCO_2$", is calculated during the re-breathing process. "During re-breathing $VCO_2$" may be calculated as the average $VCO_2$ during the interval of 25 to 30 seconds into the re-breathing period.

The content of $CO_2$ in the alveolar blood during the re-breathing process may then be calculated by employing a regression line, which facilitates prediction of the stable, or unchanging, content of alveolar $CO_2$. Preferably, $PACO_2$ is plotted against the breath-to-breath change in content of alveolar $CO_2$ ($\Delta PACO_2$). A graph line that is defined by the plotted points is regressed, and the intersection between $PACO_2$ and zero $\Delta PACO_2$ is the predicted stable content of alveolar $CO_2$.

Pulmonary capillary blood flow may then be calculated as follows:

$$Q_{pcbf} = \frac{[\text{before re-breathing } V_{CO_2} - \text{during re-breathing } V_{CO_2}]}{[\text{during re-breathing } C_A CO_2 - \text{before re-breathing } C_A CO_2]}.$$

Alternative differential Fick methods of measuring pulmonary capillary blood flow or cardiac output may be employed in place of the embodiment of the re-breathing method disclosed herein. Such alternative differential Fick methods typically require a brief change of $PetCO_2$ and $VCO_2$ in response to a change in effective ventilation. This brief change can be accomplished by adjusting the respiratory rate, inspiratory and/or expiratory times, or tidal volume. A brief change in effective ventilation may also be effected by adding $CO_2$, either directly or by re-breathing. An exemplary differential Fick method that may be employed with the present invention, which is disclosed in Gedeon, A. et al. in 18 *Med. & Biol. Eng. & Comput.* 411–418 (1980), employs a period of increased ventilation followed immediately by a period of decreased ventilation.

Estimating Shunt Fraction

After a $Q_{pcbf}$ has been determined by non-invasive means, the intrapulmonary shunt fraction of the cardiac output of the patient may be estimated. The method of estimating intrapulmonary shunt according to the present invention also includes non-invasively determining the difference between the end capillary oxygen content and the arterial oxygen content of the patient's blood, dividing the difference by the volume of carbon dioxide exhaled by the patient, and multiplying the difference by the patient's pulmonary capillary blood flow ($Q_{pcbf}$) and by the patient's respiratory quotient (RQ).

The shunt fraction of the patient's cardiac output may be derived from various respiratory profile parameters, many of which may also be measured by non-invasive techniques. $Q_s/Q_t$ may be estimated in accordance with the following equation:

$$Q_s/Q_t = \frac{Cc'O_2 - CaO_2}{Cc'O_2 - CvO_2},$$

where $Cc'O_2$ is the end-capillary oxygen content, $CaO_2$ is the arterial oxygen content, and $CvO_2$ is the mixed venous oxygen content. The denominator of the preceding formula ($Cc'O_2 - CvO_2$) can be derived from the Fick oxygen equation that has been conventionally employed in re-breathing techniques for determining cardiac output:

$$Q_{pcbf} = \frac{V_{O_2}}{Cc'O_2 - C_V O_2}.$$

$$Cc'O_2 - CvO_2 = VO_2/Q_{pcbf}$$

This equation may be rewritten as:

$$Cc'O_2 - CvO_2 = VO_2/Q_{pcbf}$$

Moreover, since the respiratory quotient (RQ) is the ratio of the carbon dioxide elimination ($VCO_2$) to the oxygen uptake ($VO_2$) of a patient, as defined by the following equation:

$$RQ = VCO_2/VO_2,$$

and because of the difficulty of accurately measuring $VO_2$, especially in patients who require an elevated fraction of inspired oxygen, and the accuracy with which RQ can be assumed (typically about 0.7 to 1.0, and more particularly about 0.8 to 0.9 or 0.86), $VCO_2/RQ$ may be substituted for $VO_2$. Thus, $$Cc'O_2 = VCO_2/(Q_{pcbf} RQ).$$

Accordingly, the shunt fraction, $Q_s/Q_t$, may be estimated, at 130 of FIG. 6, by the following formula:

$$Q_s/Q_t = \frac{\frac{Cc'O_2 - CaO_2}{V_{CO_2}}}{Q_{pcbf} \cdot RQ}.$$

$VCO_2$, which was determined above in the calculation of the pulmonary capillary blood flow of the patient, is the $CO_2$ elimination of the patient.

Alternatively, $VO_2$ may be measured as known in the art and RQ can be calculated rather than assumed. As another alternative, the $VO_2$ measurement may be divided by $Q_{pcbf}$ to directly determine $Cc'O_2 - CvO_2$, in which case the following formula may be employed to estimate the shunt fraction:

$$Q_s/Q_t = \frac{\frac{Cc'O_2 - CaO_2}{V_{O_2}}}{Q_{pcbf}}$$

The end-capillary oxygen content, $Cc'O_2$, may be calculated at 114 of FIG. 6 by the following equation:

$$Cc'O_2 = (P_AO_2 \cdot \alpha) + (Sc'O_2 \cdot Hb_{capacity} \cdot Hb_{conc}),$$

where the blood oxygen solubility coefficient ($\alpha$), end capillary blood saturation ($Sc'O_2$), hemoglobin concentration ($Hb_{conc}$) and hemoglobin capacity ($Hb_{capacity}$) values may each be assumed, or determined by known techniques, such as by direct chemical analysis of the blood.

The alveolar oxygen tension of the patient may be calculated by the following formula:

$$PAO_2 = (FiO_2 \cdot (P_{bar} - P_{H2O})) - (PaCO_2/RQ \cdot (1 - (FiO_2 \cdot (1 \cdot RQ)))).$$

where $P_{bar}$ is barometric pressure, $P_{H2O}$ is the saturated water vapor pressure of a sample at ambient temperature, and $PaCO_2$ is the partial pressure of $CO_2$ in the patient's arterial blood, which may be assumed, calculated as known in the art from non-invasively obtained arterial blood gas data, or obtained by direct measurement.

The oxygen content of the patient's arterial blood, $CaO_2$, may be calculated at 126 of FIG. 6 by the following equation:

$$CaO_2 = (PaO_2 \cdot \alpha) + (SaO_2 \cdot Hb_{capacity} \cdot Hb_{conc}).$$

Since $PaO_2$ is a function of $SaO_2$, which may be non-invasively estimated by measuring $SpO_2$ (see FIG. 6, at 124), the partial pressure of $O_2$ in the patient's arterial blood, $PaO_2$, may be calculated from the oxygen saturation ($SaO_2$) of the patient's arterial blood by employing an invertable version of a blood oxygen tension-saturation curve. Arterial blood oxygen saturation is determined non-invasively by known techniques, such as by pulse oximetry ($SpO_2$), as discussed previously in reference to FIG. 4.

Due to the inaccuracy of pulse oximetry measurements, which are typically in the range of about 2–3% and fairly consistent for a specific pulse oximeter, as well as the steepness of the tension-saturation curve between blood oxygen saturations of about 95–100%, a correction summand, which is also referred to as a correction factor, is employed in determining the oxygen saturation and partial pressure of oxygen in the arterial blood.

The correction summand may be an assumed value (e.g., 2 or 3%) based on experiential error of a known degree when a specific type of pulse oximeter or a particular model of pulse oximeter of a particular manufacturer is employed to measure $SpO_2$. Alternatively, the correction summand may be determined by comparing a direct $SaO_2$ measurement from blood gas chemical analysis with an $SpO_2$ measurement taken by a pulse oximeter.

The correction summand may then be employed in combination with subsequent pulse oximetry measurements to modify these pulse oximetry measurements and more accurately determine the partial pressure of oxygen in the patient's arterial blood. This may be done by adding a correction summand to the $SpO_2$ measurement or subtracting a correction summand from the $SpO_2$ measurement, by generating an equation to convert the $SpO_2$ measurement to a more accurate value, or by generating a special function in which the non-invasively measured, possibly somewhat inaccurate, $SpO_2$ measurement is employed to accurately determine $SaO_2$ or $PaO_2$. The $SaO_2$ or $PaO_2$ value may then be employed in the preceding equation to facilitate an accurate, non-invasive determination of the patient's intrapulmonary shunt.

In another embodiment of the method of estimating intrapulmonary shunt, the $SaO_2$ or $PaO_2$ of a patient may be non-invasively determined and corrected as described above. The patient's $FiO_2$ is also determined, as known in the art, such as by a respiratory measurement or from a set fraction, or value, of oxygen in a gas mixture with which the patient is artificially ventilated. An iso-shunt diagram, which is also referred to as an iso-shunt plot, such as that disclosed in S. R. Benatar et al., The use of iso-shunt lines for control of oxygen therapy, Brit. J Anaesth. (1973) 45:711, and in NUNN, J. F., NUNN's APPLED RESPIRATORY PHYSIOLOGY 184, FIG. 8.10 (4th ed.) and shown in FIG. 7, may then be employed with the $SaO_2$ or $PaO_2$ and $FiO_2$ measurements to determine the intrapulmonary shunt fraction of the cardiac output of the patient.

Figure 7:
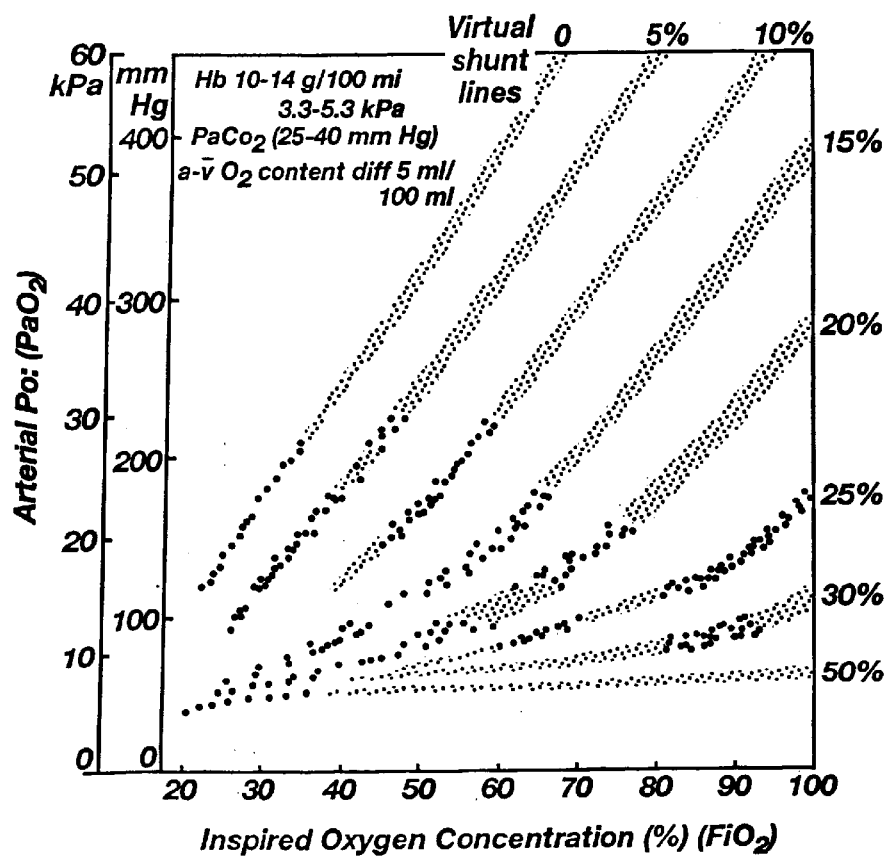
FIG. 7 is an iso-shunt diagram that is useful in determining the intrapulmonary shunt fractions of the cardiac output of a patient in accordance with another embodiment of the methods.
Figure 8:
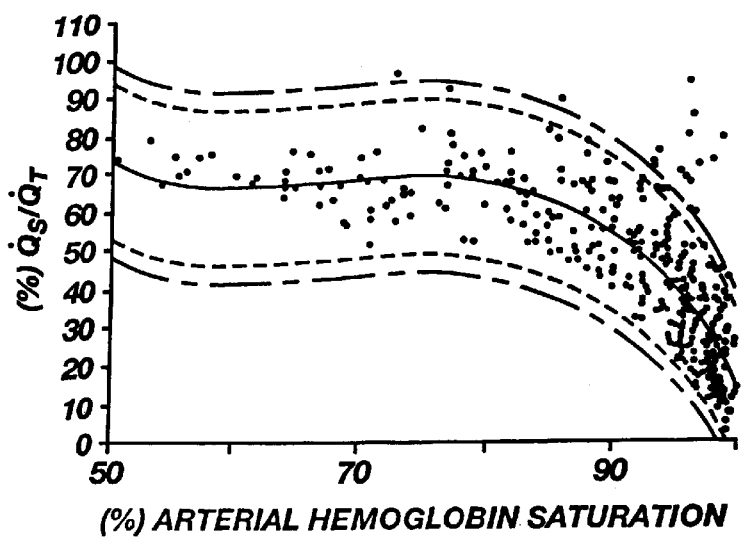
FIG. 8 is another iso-shunt diagram that may be employed to determine the intrapulmonary shunt fraction of the cardiac output of a patient.

The intrapulmonary shunt fraction may be similarly estimated by incorporating the measured $SaO_2$ or $PaO_2$ and $FiO_2$ values into the following series of equations that Nunn used to generate the iso-shunt diagram of FIG. 7 from $FiO_2$ and $PaO_2$ measurements:

$$PAO_2 = ((P_{bar} - P_{H2O}) \cdot FiO_2) - (PaCO_2 RQ)(1 - FiO_2 \cdot (1 - RQ)),$$

where $PaO_2$ is the partial pressure of oxygen in the alveoli of the patient; $P_{bar}$, the barometric pressure, is assumed to be 101.33 kPa; $P_{H2O}$, or water pressure, is assumed to be 6.27 kPa; $PaCO_2$, the partial pressure of carbon dioxide in the arterial blood of the patient, or the arterial carbon dioxide tension, is assumed to be 5.33 kPa; and RQ is assumed to be 0.8 (alternatively, each of these parameters may be assumed to be equal to a different value or measured by techniques known in the art);

$$ScO_2=(PAO_2^3+2.667 \cdot PAO_2)/(PAO_2^3+2.667 \cdot PAO_2+55.47),$$

or the Severinghaus equation for conversion from partial pressure of oxygen to oxygen saturation, where $ScO_2$ is the oxygen saturation of the end capillary blood of the patient; other equations for converting partial pressure of oxygen to oxygen saturation, such as the Lobdell equation, may also be employed;

$$Cc'_2=(PAO_2 \cdot \alpha)+(ScO_2 \cdot Hb_{cap} \cdot Hb_{conc}),$$

where $Hb_{cap}$ is assumed to be 1.31 (ml/g) and $Hb_{conc}$ is assumed to be 14 g/dl;

$$SaO_2=(1 \cdot PaO_2^3+2.667 \cdot PaO_2+55.47),$$

or the Severinghaus equation for conversion from partial pressure of oxygen to oxygen saturation, where $SaO_2$ is the oxygen saturation of the arterial blood of the patient and $PaO_2$ is the partial pressure of oxygen in the arterial blood of the patient; other equations for converting partial pressure of oxygen to oxygen saturation, such as the Lobdell equation, may also be employed;

$$CaO_2=(PaO_2 \cdot \alpha)+(SaO_2 \cdot Hb_{cap} \cdot Hb_{conc}),$$

where $Hb_{cap}$ is assumed to be 1.31 (ml/g) and $Hb_{conc}$, is assumed to be 14 g/dl; and $$Q_s/Q_t=100 \cdot (Cc'O_2-Ca'O_2)/((CaO_2-CvO_2)+(Cc'O_2)),$$

where ($CaO_2-CvO_2$), the arterial-venous oxygen gradient of the patient, is assumed to remain substantially constant over short periods of time (e.g., one, five, or ten minutes).

Other iso-shunt equations or diagrams are also useful with the corrected $SaO_2$ and $PaO_2$ values of the present invention to estimate the intrapulmonary shunt of a patient, such as the equation and graphs disclosed in Dean, J. M., Wetzel, R. C., and Rogers, M. C., Arterial blood gas derived variables as estimates of intrapulmonary shunt in critically ill children, *Crit. Care Med.* 13(12):1029–1033 (1985)("Dean"). The equation of Dean:

$$Q_s/Q_t = \frac{(Hgb)(1.34)(1 - SaO_2)}{((Hgb)(1.34)(1 - SaO_2) + (CaO_2 - C_VO_2))},$$

where Hgb is the hemoglobin concentration of the patient, may be employed to estimate the intrapulmonary shunt fraction of the cardiac output of the patient. Alternatively, $SaO_2$ may be employed with the graph of FIG. 8, which is depicted in Dean, to estimate the intrapulmonary shunt fraction.

Other exemplary equations and diagrams that may be employed with the $SaO_2$ or $PaO_2$ values determined in accordance with the present invention to estimate the intrapulmonary shunt fraction of the cardiac output of a patient are disclosed in Hope, D.A. et al., Non-invasive estimation of venous admixture: validation of a new formula, *Brit. J Anaesth.* (1995) 74:538–543 and Sapsford, D. J. and Jones, J. G., The $PiO_2$ vs. $SpO_2$ diagram: a non-invasive measure of pulmonary oxygen exchange, *Eur. J Anaesth.* (1995) 12:375–386.

When a non-invasive pulmonary capillary blood flow ($Q_{pcbf}$) has been determined and the shunt fraction ($Q_s/Q_t$) estimated, the patient's cardiac output ($Q_t$) may be determined.

Calculating Cardiac Output

The patient's cardiac output may be determined by adding the non-invasively measured volumetric rate of pulmonary capillary blood flow ($Q_{pcbf}$) and the volumetric rate of flow of the patient's shunted blood ($Q_s$) by the following equation:

$$Q_t=Q_{pcbf}+Q_s$$

Alternatively, the preceding equation may be re-written so that a patient's total cardiac output may also be determined from the shunt fraction ($Q_s/Q_t$) and pulmonary capillary blood flow as follows:

$$Q_t=Q_{pcbf}/(1-Q_s/Q_t).$$

Although the foregoing description contains many specifics, these should not be construed as limiting the scope of the present invention, but merely as providing illustrations of some of the presently preferred embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions and modifications to the invention as disclosed herein which fall within the meaning and scope of the claims are to be embraced thereby.

What is claimed is:

1. A method of estimating a cardiac output of a patient, comprising:

determining an oxygen saturation of arterial blood of the patient;

determining a fraction of inspired oxygen of the patient;

determining a pulmonary capillary blood flow of the patient; and determining an intrapulmonary shunt fraction from said oxygen saturation and said fraction of inspired oxygen.

2. The method of claim 1, wherein said determining said intrapulmonary shunt fraction comprises employing an iso-shunt plot.

3. The method of claim 1, wherein said determining said intrapulmonary shunt fraction comprises calculating said intrapulmonary shunt fraction with an iso-shunt equation.

4. The method of claim 1, wherein said determining said intrapulmonary shunt fraction further comprises employing said pulmonary capillary blood flow.

5. The method of claim 1, further comprising calculating the cardiac output with said intrapulmonary shunt fraction and said pulmonary capillary blood flow.

6. The method of claim 1, further comprising calculating an intrapulmonary shunt flow of the patient with said intrapulmonary shunt fraction and said pulmonary capillary blood flow.

7. The method of claim 6, further comprising calculating the cardiac output with said intrapulmonary shunt flow and said pulmonary capillary blood flow.

8. The method of claim 1, wherein said determining said pulmonary capillary blood flow comprises re-breathing.

9. The method of claim 8, wherein said re-breathing comprises total or partial re-breathing.

10. The method of claim 1, wherein said determining said pulmonary capillary blood flow comprises adjusting a respiratory rate.

11. The method of claim 1, wherein said determining said pulmonary capillary blood flow comprises adjusting a period of inspiration or expiration.

12. The method of claim 1, wherein said determining said pulmonary capillary blood flow comprises adjusting a tidal volume.

13. The method of claim 1, wherein said determining said pulmonary capillary blood flow comprises adding a volume of carbon dioxide to ventilation of the patient.

14. The method of claim 1, further comprising correcting said oxygen saturation of arterial blood.

15. The method of claim 14, wherein said correcting comprises generating a correction summand and modifying said oxygen saturation of arterial blood by said correction summand.

16. The method of claim 15, wherein said generating comprises selecting an assumed value.

17. The method of claim 16, wherein said assumed value comprises about 2% to 3% of said oxygen saturation of arterial blood.

18. The method of claim 16, wherein said generating comprises directly obtaining another measurement of arterial oxygen saturation of arterial blood and comparing said another measurement to said oxygen saturation of arterial blood.

19. The method of claim 16, wherein said generating comprises generating an equation for converting said oxygen saturation of arterial blood to a substantially accurate value.

20. The method of claim 1, wherein said determining said oxygen saturation of arterial blood comprises non-invasively determining said oxygen saturation of arterial blood.

21. The method of claim 20, wherein said non-invasively determining said oxygen saturation of arterial blood is effected by a technique comprising pulse oximetry.

22. The method of claim 1, wherein said determining said fraction of inspired oxygen comprises measuring an oxygen fraction of respiration of the patient.

23. The method of claim 1, wherein said determining said fraction of inspired oxygen comprises a set fraction of oxygen with which the patient is artificially ventilated.

24. The method of claim 1, further comprising determining an end capillary blood oxygen content of the patient.

25. The method of claim 24, wherein said determining said end capillary blood oxygen content comprises employing an end tidal oxygen partial pressure of respiration of the patient.

26. The method of claim 24, wherein said determining said end capillary blood oxygen content comprises employing an end tidal carbon dioxide partial pressure of respiration of the patient.

27. A method of determining a cardiac output of a patient, comprising:

determining a respiratory flow and a respiratory carbon dioxide content of gas mixtures inhaled and exhaled by the patient;

calculating a first carbon dioxide elimination and a first alveolar carbon dioxide content of the patient;

conducting a re-breathing process on the patient's breathing;

calculating a second carbon dioxide elimination and a second alveolar carbon dioxide content of the patient during said conducting;

estimating a pulmonary capillary blood flow of the patient;

non-invasively determining an arterial blood oxygen content of the patient; estimating an intrapulmonary shunt of the patient; and calculating the cardiac output from said estimated intrapulmonary shunt and said estimated pulmonary capillary blood flow.

28. The method of claim 27, further comprising correcting for an inaccuracy of said arterial blood oxygen content.

29. A method of estimating an intrapulmonary shunt fraction of a cardiac output of a patient, comprising:

determining an oxygen saturation of arterial blood of the patient;

determining a fraction of inspired oxygen of the patient;

determining a pulmonary capillary blood flow of the patient; and employing said oxygen saturation of arterial blood and said fraction of inspired oxygen to determine the intrapulmonary shunt fraction of said pulmonary capillary blood flow.

30. The method of claim 29, wherein said determining said pulmonary capillary blood flow comprises re-breathing.

31. The method of claim 30, wherein said re-breathing comprises partial or total re-breathing.

32. The method of claim 29, wherein said employing comprises employing said oxygen saturation of arterial blood and said fraction of inspired oxygen with at least one of an iso-shunt plot and an iso-shunt equation.

33. The method of claim 29, wherein said determining said pulmonary capillary blood flow comprises adjusting a respiratory rate.

34. The method of claim 29, wherein said determining said pulmonary capillary blood flow comprises adjusting a period of inspiration or expiration.

35. The method of claim 29, wherein said determining said pulmonary capillary blood flow comprises adjusting a tidal volume.

36. The method of claim 29, wherein said determining said pulmonary capillary blood flow comprises adding a volume of carbon dioxide to ventilation of the patient.

37. The method of claim 29, wherein said determining said oxygen saturation of arterial blood comprises obtaining a pulse oximetry measurement and converting said pulse oximetry measurement to said oxygen saturation of arterial blood.

38. The method of claim 37, further comprising generating a correction summand for said oxygen saturation of arterial blood.

39. The method of claim 38, wherein said correction summand comprises an assumed value.

40. The method of claim 38, wherein said generating comprises directly obtaining another measurement of oxygen saturation of arterial blood and comparing said another measurement to said oxygen saturation of arterial blood.

41. The method of claim 38, wherein said generating comprises generating an equation for converting said oxygen saturation of arterial blood to a substantially accurate value.

42. The method of claim 35, wherein said determining said fraction of inspired oxygen comprises measuring said fraction of inspired oxygen.

43. The method of claim 32, wherein said fraction of inspired oxygen comprises a set fraction of oxygen with which the patient is artificially ventilated.

* * * * *

UNITED STATES PATENT AND TRADEMARK OFFICE
CERTIFICATE OF CORRECTION

PATENT NO. : 6,258,038 B1
DATED : July 10, 2001
INVENTOR(S) : Haryadi et al.

It is certified that error appears in the above-identified patent and that said Letters Patent is hereby corrected as shown below:

<u>Title page,</u>
Item [56], References Cited,
FOREIGN PATENT DOCUMENTS, change "(WO)" to -- WIPO --;
OTHER PUBLICATIONS, after "237" delete ","; after "tion" delete "."; change after "#234" delete ","; and change "Pulimonary" to -- Pulmonary --.

<u>Column 9,</u>
Line 15, in the equation, change "®" to -- (r --;
Line 15, at the end of equation, change "." to -- , --;
Line 34, in the equation change "=94.864" to -- +94.864 --;

<u>Column 10,</u>
Line 67, delete entire equation (duplicate of equation and text appearing at top of column 11);

<u>Column 11,</u>
Line 21, change beginning of equation "$Cc'O_2=$" to -- $Cc'O_2-CvO_2=$ --;
Line 62, at the end of equation change "." to -- , --;

<u>Column 12,</u>
Line 8, change "invertable" to -- invertible --;

<u>Column 13,</u>
Line 19, in equation change "$Hb_{cap}Hb_{conc}$" to -- $Hb_{cap} \cdot Hb_{conc}$ --;
Line 25, in equation change "$PaO_2+55.47)$" to -- $PaO_2)/(1 \cdot PaO_2^3+2.667 \cdot PaO_2+55.47)$, --;
Line 41, in equation change "$(Cc'O_2))$" to -- $(Cc'O_2- CaO_2))$ --; and <u>Column 14,</u>
Line 20, at the end of equation insert -- . --.

UNITED STATES PATENT AND TRADEMARK OFFICE
CERTIFICATE OF CORRECTION

PATENT NO. : 6,258,038 B1
DATED : July 10, 2001
INVENTOR(S) : Haryadi et al.

It is certified that error appears in the above-identified patent and that said Letters Patent is hereby corrected as shown below:

Column 15,
Line 4, change "determ ining" to -- determining --;
Lines 32-33, delete "arterial"; and Column 16,
Line 14, after "patient;" insert {hard return} and start text beginning with "estimating" on Line 15 as an indented paragraph.

Signed and Sealed this

Twenty-fourth Day of September, 2002

Attest:

JAMES E. ROGAN
Attesting Officer  Director of the United States Patent and Trademark Office

UNITED STATES PATENT AND TRADEMARK OFFICE
CERTIFICATE OF CORRECTION

PATENT NO. : 6,258,038 B1
DATED : July 10, 2001
INVENTOR(S) : Haryadi et al.

It is certified that error appears in the above-identified patent and that said Letters Patent is hereby corrected as shown below:

Title page,
Item [56], References Cited,
FOREIGN PATENT DOCUMENTS, change "(WO)" to -- WIPO --;
OTHER PUBLICATIONS, after "237" delete ",";
After "tion" delete ".";
Change after "#234" delete ","; and
Change "Pulimonary" to -- Pulmonary --.

Column 9,
Line 15, in the equation, change "®" to -- (r --;
Line 15, at the end of equation, change "." to -- , --;
Line 34, in the equation change "=94.864" to -- +94.864 --;

Column 10,
Line 67, delete entire equation (duplicate of equation and text appearing at top of column 11);

Column 11,
Line 21, change beginning of equation "Cc'O$_2$=" to -- Cc'O$_2$-CvO$_2$= --;
Line 62, at the end of equation change "." to -- , --;

Column 12,
Line 8, change "invertable" to -- invertible --;

Column 13,
Line 19, in equation change "Hb$_{cap}$Hb$_{conc}$" to -- Hb$_{cap}$·Hb$_{conc}$ --;
Line 25, in equation change "PaO$_2$+55.47)" to -- PaO$_2$)/(1·PaO$_2^3$+2.667·PaO$_2$+55.47), --;
Line 41, in equation change "(Cc'O$_2$))" to -- (Cc'O$_2$- CaO$_2$)) --; and Column 14,
Line 20, at the end of equation insert -- . --.

UNITED STATES PATENT AND TRADEMARK OFFICE
CERTIFICATE OF CORRECTION

PATENT NO. : 6,258,038 B1
DATED : July 10, 2001
INVENTOR(S) : Haryadi et al.

It is certified that error appears in the above-identified patent and that said Letters Patent is hereby corrected as shown below:

Column 15,
Line 4, change "determ ining" to -- determining --;
Lines 32-33, delete "arterial"; and Column 16,
Line 14, after "patient;" insert {hard return} and start text beginning with "estimating" on Line 15 as an indented paragraph.

Signed and Sealed this

Fifteenth Day of October, 2002

*Attest:*

JAMES E. ROGAN
*Attesting Officer*       *Director of the United States Patent and Trademark Office*